(12) United States Patent
Mathieu et al.

(10) Patent No.: US 10,194,700 B2
(45) Date of Patent: Feb. 5, 2019

(54) SELF-ADHESIVE POSTURE AND SPLINTING BAND IN PARTICULAR FOR COMPRESSION STOCKING

(75) Inventors: Florence Mathieu, Saint-Galmier (FR); Gaetan Romuald, Lyons (FR)

(73) Assignee: Ganzoni & Cie AG, St. Gallen (CH)

( * ) Notice: Subject to any disclaimer, the term of this patent is extended or adjusted under 35 U.S.C. 154(b) by 383 days.

(21) Appl. No.: 12/989,887

(22) PCT Filed: Apr. 24, 2009

(86) PCT No.: PCT/FR2009/050760
§ 371 (c)(1),
(2), (4) Date: Jan. 19, 2011

(87) PCT Pub. No.: WO2009/138672
PCT Pub. Date: Nov. 19, 2009

(65) Prior Publication Data
US 2011/0112459 A1    May 12, 2011

(30) Foreign Application Priority Data

Apr. 30, 2008 (FR) ..................... 08 52909

(51) Int. Cl.
*A41B 11/12* (2006.01)
*A61F 13/08* (2006.01)

(52) U.S. Cl.
CPC ............ *A41B 11/126* (2013.01); *A61F 13/08* (2013.01)

(58) Field of Classification Search
CPC .... A61L 15/00; A61F 13/02; A61F 13/00017; A61F 13/00; A61F 13/00119;
(Continued)

(56) References Cited

U.S. PATENT DOCUMENTS 5,497,513 A * 3/1996 Arabeyre ............... A61F 13/08
 2/16
6,059,834 A * 5/2000 Springs ................ A61F 2/7812
 602/63
(Continued)

FOREIGN PATENT DOCUMENTS

EP  1 079 017 A  2/2001
FR  1 540 295 A  9/1968
(Continued)

OTHER PUBLICATIONS

Murayama, Takayuki; "Dynamic Mechanical Analysis of Polymeric Materials"; Elsevier Scientific Publishing CO.; 1982.*
(Continued)

*Primary Examiner* — Ophelia A Hawthorne
*Assistant Examiner* — Caitlin Carreiro
(74) *Attorney, Agent, or Firm* — Heslin Rothenberg Farley & Mesiti P.C.

(57) ABSTRACT

A self-adhesive band or complex has a textile support structure with a coating for securing to the skin of a wearer. The textile support structure includes an extensible, aerated, finely knitted or woven support structure having, at least on its inner face, a thin coating having immediate and high adhesive properties. The coating has a degree of softness to conform to microreliefs of the wearer's skin, and an elastic modulus at least as low as that of the substrate against which it is in contact to match the microreliefs thereof.

11 Claims, 2 Drawing Sheets

(58) Field of Classification Search
CPC .......... A61F 13/00029; A61F 13/00174; A61F 13/00038; A61F 13/0269; A61F 13/0273
USPC ....... 602/44, 52, 55; 523/111, 118; 428/193, 428/213, 214
See application file for complete search history.

(56) References Cited

U.S. PATENT DOCUMENTS

| | | | | |
|---|---|---|---|---|
| 6,495,229 | B1* | 12/2002 | Carte | A61F 13/023 428/40.1 |
| 7,854,716 | B2* | 12/2010 | Schuren et al. | 602/75 |
| 2004/0092855 | A1* | 5/2004 | Fabo | 602/51 |
| 2007/0140991 | A1* | 6/2007 | Maitra | A61K 8/8152 424/53 |
| 2009/0112141 | A1* | 4/2009 | Derr | 602/53 |

FOREIGN PATENT DOCUMENTS

| | | |
|---|---|---|
| FR | 2 887 124 A | 12/2006 |
| WO | 98/002120 A | 1/1998 |
| WO | 2004/082935 A | 9/2004 |

OTHER PUBLICATIONS

"definelace-googlesearch.pdf"; definition of "lace": (Google Search); accessed Feb. 22, 2015.*
Murayama, Takayaki; "Dynamic Mechanical Analysis of Polymeric Material"; Elsevier Scientific Publishing Co (1982).*
Dow Corning pamphlet: "medical device silicone adhesives"; accessed from www.dowcorning.com.*
"Dynamic Mechanical Analysis of Polymeric Materials".*
Dow Corning—"Medical Device Silicone Adhesives".*
Takayaki Murayama—"Dynamic Mechanical Analysis of Polymeric Material".*
Takayaki Murayama: "Dynamic Mechanical Analysis of Polymeric Materials".*
"Medical Device Silicone Adhesives" (Dow Corning).*
International Search Report for PCT/FR2009/050760, dated Dec. 15, 2009.

* cited by examiner

SELF-ADHESIVE POSTURE AND SPLINTING BAND IN PARTICULAR FOR COMPRESSION STOCKING

CROSS REFERENCE TO RELATED APPLICATIONS

This application is a national stage filing under section 371 of International Application No. PCT/FR2009/050760, filed on Apr. 24, 2009, and published in French on Nov. 19, 2009, as WO2009/138672 and claims priority of French application No. 0852909 filed on Apr. 30, 2008, the entire disclosure of these applications being hereby incorporated herein by reference.

BACKGROUND ART

The invention relates to the technical field of posture and splinting bands, and also of compression stockings and socks, using for compression an upper or overlapping end, with coatings in contact with the wearer's skin.

In its principle, this concept has been known for many years, in particular for stockings to be secured around the wearer's thigh or calf, according to its purpose.

Numerous patents have been filed by numerous manufacturers with, at the outset, French patent FR 1.540.295, followed by many others.

The use of a silicone coating is thus known for applications to stockings and socks, for normal use, and also for splinting, compression and posture.

The products available on the market have, according to each case, a number of drawbacks related to putting them on and taking them off.

A first drawback resides in the fact that the compression effect on the wearer's member, even in the absence of necking, and because of the contact and the wearer's movements, causes friction and shear effects, which engender unpleasant and ultimately painful irritations. This is due to the texture of the support and to a certain stiffness of the coating.

Even when the skin is not particularly sensitive to chemical or allergenic agents, it risks being irritated by the wearing of a self-adhesive band if the following two or three conditions are combined: bacterial proliferation, friction, maceration.

As to friction, the irritation is mechanical due to the difference in mechanical behaviour between the support and its coating and the skin.

The risk of irritation increases with age (thinner and more fragile skin). It is therefore indispensable to protect the skin of an elderly person because it is regenerated more slowly.

The risk also increases:

with heat, summer in particular, due to sweating;

during intensive physical activity, movement and sweating.

Maceration results from the fragilization of the skin (lower mechanical strength) and the increase in permeability, hence lower resistance to pathogenic agents and chemical irritants. This maceration is caused by a lack of evaporation of the water vapour (perspiration) naturally emitted by the skin, entailing the need for the product to be permeable to water vapour.

Another drawback observed during the wearing of a self-adhesive band is that of the distribution of the hair of the members on which it is to be worn, because this gives rise to friction, and the irritation and discomfort are commensurately greater. The maintenance of the stocking or the band, by an adhesive having a high adhesiveness (such as adhesive plaster), would also make their removal very painful due to the pulling force.

It is based on these findings that the applicant has sought a novel type of self-adhesive band serving to eliminate the friction and to considerably reduce the risk of maceration and hence of skin irritation.

Secondarily, a further goal was to improve the wearer's comfort and the conditions of removal of the self-adhesive band or stocking by reducing the induced effects, particularly of the hair pulling type.

Another approach of the applicant was therefore to improve the wearer's comfort with a lighter product, that is, having a finer visual appearance than the products on the market.

It was therefore necessary to design a novel self-adhesive band offering controlled compression, optimised behaviour, while reducing the various risks and situations promoting skin irritation.

In fact, numerous investigations have been conducted with control tests to improve a variety of particular parameters.

In practice, this type of investigation has not proved conclusive to the best of the applicant's knowledge.

BRIEF SUMMARY OF INVENTION

According to the invention, a comprehensive approach was pursued, both in the choice of the support and of the coating, allowing the design of a self-adhesive band offering an optimization of the effects, achieved by a very particular selection of its components, contributing unexpected indirect advantages in putting on and taking off in case the wearer has a high hair distribution.

According to a first feature of the invention, the self-adhesive band or complex is of the type comprising a textile structure with a silicone coating for securing to the skin of a wearer, the band being characterized in that the support portion of the coating is prepared in the form of a knitted or woven support, which can be extensible, which comprises at least on its inner surface a coating having immediate and high tack properties, and in that the coating is defined with a degree of softness to conform to the microreliefs of the substrate such as the wearer's skin, and in that the elastic modulus of the coating is defined to be at least as low as that of the substrate against which it is in contact to match the microdeformations thereof, and in that the coating is applied in a thin layer on the support portion, which is itself fine and aerated.

According to another feature, the support portion of the band is prepared in the form of a lace.

Thus, the self-adhesive band, according to the invention, defines an extensible elastic complex having an adhesiveness and particular physical or chemical and mechanical properties, in order to have controlled compression and optimised behaviour on the member, while reducing or eliminating the risk of skin irritation.

Thus, according to the invention, this self-adhesive band may be applied to compression stockings and socks or another splinting or compression article of the bandage type.

These features and others will appear clearly from the rest of the description.

BRIEF DESCRIPTION OF THE DRAWING FIGURES

The object of the invention is illustrated in the figures of the drawings in which.

DETAILED DESCRIPTION

To express the object of the invention more concretely, it is now described in a non-limiting manner illustrated in the figures of the drawings.

Figure 1:
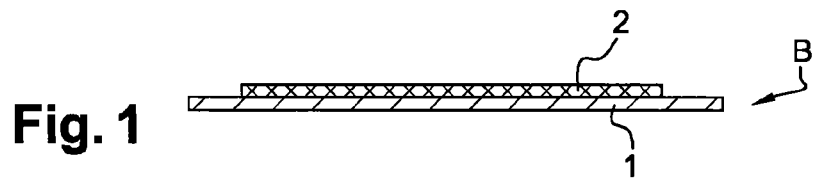
FIG. 1 shows a partial view of a self-adhesive band, according to the invention, in its single-face version.
Figure 2:
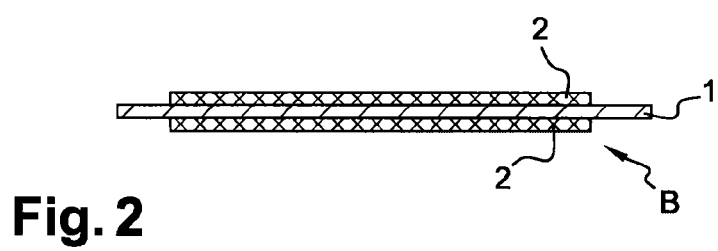
FIG. 2 shows a partial view of the self-adhesive band in its double-face version.
Figure 3:
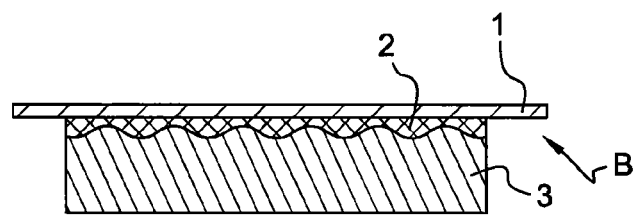
FIG. 3 shows a large scale partial view showing one of the advantages of the invention in the configuration in which the coating closely matches the apparent rough shapes of the substrate, when the latter is the skin of a wearer, for example.

The self-adhesive band (B) of the complex comprises a textile structure (1), constituting the support, and prepared in the form of a knitted or woven support having physical properties (elasticity, extensibility, surface condition, roughness, thickness and permeability). This support, according to the intended applications, for example as a compression or posture stocking, is prepared in the form of a lace. This textile structure, as shown in FIGS. 1 and 2 of the drawings, can be made in a single-face or double-face form and includes at least, on its inner face and also, as an alternative, on both its inner and outer faces, a coating (2), having immediate and high tack properties. More particularly, the adhesive layer or layers obtained by the coating have a thickness of about 0.5 mm. The particular properties of this coating are its immediate adhesiveness combined with its softness, called, in professional technical terms, "tack", its viscoelasticity, its water vapour transmission rate and its biocompatibility. This coating on the inner and/or outer faces of the textile structure is defined with a degree of softness to conform to and match the microreliefs of the substrate (3) such as the wearer's skin. Furthermore, the elastic modulus of the coating is defined to be at least as low as that of the substrate against which it is in contact to match the microdeformations thereof.

The coating may be a mono- or multi-component coating. According to the invention, it has a high tack and consists of a water-repellent adhesive that is sensitive to pressure. The tack properties, tack energy and force, are measured by a tack probe test and a dynamic mechanical analysis on DMA Q800. This adhesive may be of the polyurethane, silicone, Styrene-Isoprene-Styrene and Styrene-Butadiene-Styrene type. In an advantageous example, the coating employs two silicone compositions developed by Momentive Performance Materials Inc. under reference RTV 833, with the use of a first RTV 833A component, that is a polydimethylsiloxane with vinyl groups and platinum catalyst, and a second RTV 833B, with a mixture of polydimethylsiloxanes, sealants, and crosslinking agent. The softness is measured by pressure. The adhesiveness of the coating is obtained by the grammage of the coating and the proportions and batchings of the components, one or more adhesive resins possibly being added. Silicone and polyurethane are advantageously used because of their high permeability to water vapour.

The coating is preferably made in the form of a film in order to have the most uniform possible distribution on the support. While remaining within the scope of the invention, it may be obtained in a continuous or discontinuous configuration. The self-adhesive band or complex obtained has a low thickness, about 1 mm and a coating thickness of 0.5 mm. The thickness of the coating may vary. The grammage of the coating is lower than 500 g/m$^2$. Due to the porosity of the textile structure constituting the support in order to facilitate the curing of the coating, the water vapour transmission rate is at least 30% higher than that of conventional self-adhesive bands, essentially due to the choice of the type of support and the reduced thickness of the coating.

The self-adhesive band used according to the invention has been the subject of various comparative tests with previous products of the applicant, and products of third party manufacturers. The basis of comparison and testing is the applicant's prototype F5001 corresponding to the requisite standards for taking measurements.

The table below defines the extensibility of the self-adhesive bands. It may be observed that all the self-adhesive bands currently on the market have 40 to 110% higher compression for 30% elongation compared to the prototype "F5001", the reference basis.

| Product Name | Manufacturer | ACL Code | Size | Compression Class | Lace Width (cm) | Lace Flat Dim (cm) | Lace Dim Stretched 30% (cm) | Compression at 30% elongation (hPa) | Compression at 30% elongation (hPa/cm) | Differential/ SIG TACK/F 5001 |
|---|---|---|---|---|---|---|---|---|---|---|
| Mediven Elegance Autofix Platinum | Medi | 4654052 | Small long | 2 | 5.4 | 19.7 | 25.61 | 18.21 | 3.37 | 116.79 |
| Mediven Seduction | Medi | 4466617 | Small Court | 1 | 5.4 | 19.3 | 25.09 | 12.07 | 2.24 | 43.69 |
| Varisma Seduction | Innothera | 4458925 | T1 normal | 2 | 6.6 | 19.5 | 25.35 | 13.02 | 1.97 | 55.00 |
| Venactif Reflets de teint | Gibaud | 4592322 | 1 | 2 | 5.5 | 18.7 | 24.31 | 12.1 | 2.20 | 44.05 |
| Venaflex Secret | Thuasne | 4347611 | 1N | 2 | 6.7 | 18.1 | 23.53 | 16 | 2.39 | 90.48 |
| Voile Radiante | Cognon Morin | 4554959 | 1M | 2 | 4.8 | 19.1 | 24.83 | 15.14 | 3.15 | 80.24 |
| Velinostim Déesse | Pierre Fabre | 4536826 | T1 Normal | 2 | 6 | 17.5 | 22.75 | 12.79 | 2.13 | 52.26 |

-continued

| Product Name | Manufacturer | ACL Code | Size | Compression Class | Lace Width (cm) | Lace Flat Dim (cm) | Lace Dim Stretched 30% (cm) | Compression at 30% elongation (hPa) | Compression at 30% elongation (hPa/cm) | Differential/ SIG TACK/F 5001 |
|---|---|---|---|---|---|---|---|---|---|---|
| F 5001 | Sigvaris | TR 125-1 | SN | 2 | 5.4 | 20.6 | 26.78 | 8.4 | 1.56 | 0.00 |
| Nelly | Sigvaris |  | SL | 2 | 5.2 | 20.7 | 26.91 | 6.83 | 1.31 | −18.69 |
| Diaphane | Sigvaris | 7974314 | SN | 2 | 5.6 | 20.8 | 27.04 | 12.36 | 2.21 | 47.14 |

The figures of the drawings show the self-adhesive band in its single-face version (FIG. 1) in contact with the substrate or skin and the double-face version (FIG. 2).

Figure 4:
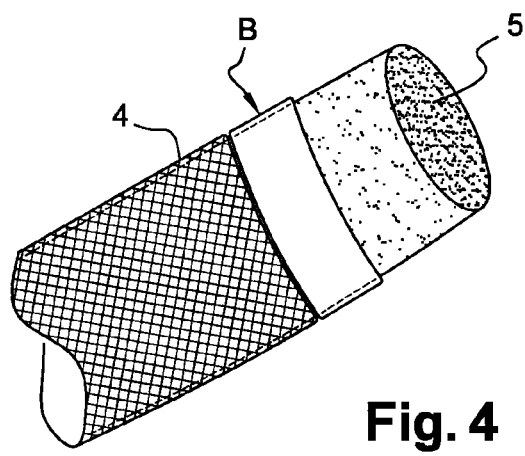
FIG. 4 shows a view of an exemplary embodiment of the self-adhesive band according to the invention in its single face version and applied to a medical splinting and/or compression stocking.

In FIG. 4, the self-adhesive band which is made from a textile structure prepared in lace is prolonged by the medical lower portion (4) or sleeve slipped on a member (5) of the wearer.

Figure 5:
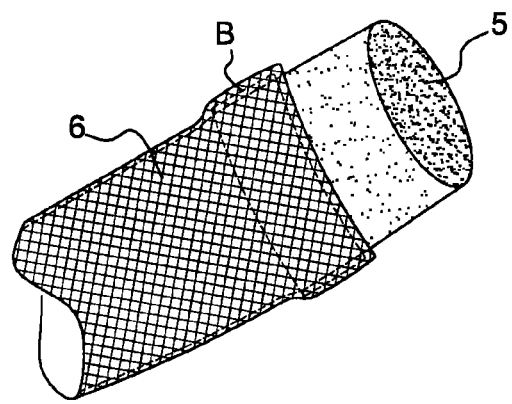
FIG. 5 shows a view of an exemplary embodiment of the self-adhesive band in its double-face version, with a compression and/or splinting device.

In FIG. 5, the self-adhesive band is double-faced and is adapted to a compression/splinting device (6).

Figure 6:
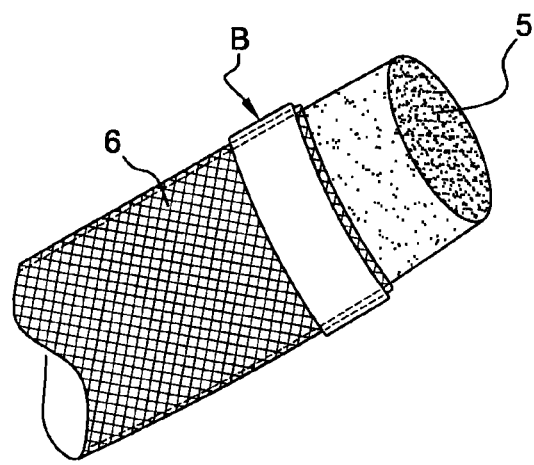
FIG. 6 shows an exemplary embodiment of the self-adhesive band in a single-face version, which is placed in a compression and/or splinting device.

In FIG. 6, the self-adhesive band of the invention is adapted to a compression/splinting device (6), while allowing an overlapping border of the latter to appear.

Figure 7:
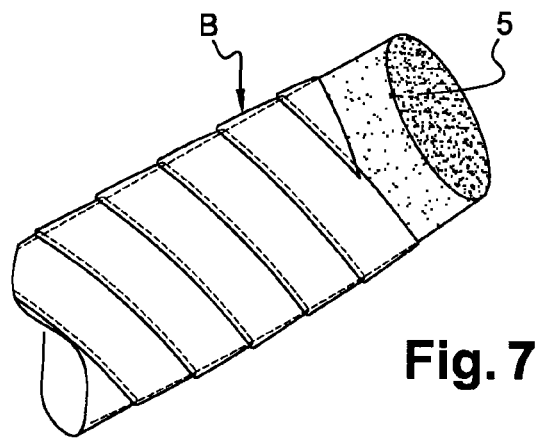
FIG. 7 shows an exemplary embodiment of the self-adhesive band in a wrapping configuration.

In FIG. 7, the single-face self-adhesive band itself constitutes a bandage wrapped in turns for the partial overlap.

While remaining within the scope of the invention, the coating may incorporate hydrophilic substances in the form of fillers (hydrocolloids, pectin, etc.) or micro-capsules with controlled salting out to provide a supplementary function or treatment (bacteriostatic, bactericidal, anti-inflammatory, cicatrizer, moisturizing, etc.).

The self-adhesive band, according to the invention, offers optimised comfort and behaviour, due to its particular features, while eliminating or reducing all the initial drawbacks identified which generate pain, and irritation to the skin.

The adhesiveness of the coating is sufficient for the self-adhesive band to remain in place without any other means.

The easy removal of the self-adhesive band is painless, without any residue, and is also effective in a situation with high hair distribution. This easy removal is measured by a peeling test at 180° performed on a glass substrate according to standard NF EN 28510-2 after 24 h of maintenance. Although the coating has a high tack, the peeling force is not high. The latter is substantially equivalent to that of a conventional coating, and in any case remains low, <0.6 N/nm.

The self-adhesive band, due to the combination of its features, serves to avoid friction, a source of irritation, while helping to match the microdeformations of the skin associated with its relief and its own extensibility, and the macrodeformations associated with body movements. The absence of residue on removal is due to the cohesion of the coating confirmed during the 180° peeling test. The test probe serves to determine the tack energy and force, which for the coating of the invention, has a tack energy of at least 3.8 N·mm (<3.0 for a conventional coating) and a tack force at least 8N (compared to 4N for a conventional coating). The DMA (dynamic mechanical analysis) serves to determine the moduli G' and G" correlated with the tack properties. The slopes are significantly higher on the coating of the invention:
- slope log G'>=0.2 (compared to 0.05 for a conventional coating),
- slope log G">=0.24 (compared to 0.15 for a conventional coating).

The invention claimed is:

1. A compression stocking for applying compression to a body member, including an upper ring shaped self-adhesive band consisting of a textile support structure with a tacky coating for securing the band directly to skin of a wearer, the textile support structure comprising an extensible, elastic, aerated, finely knitted or woven textile support structure configured for encircling and providing controlled compression to the body member, and having, at least on an inner surface, said tacky coating configured to be ring shaped when positioned on the body member and consisting of a single, solid, un-interrupted adhesive layer in the form of a film continuously applied and having continuous adhesive properties along a height of the band, the coating comprising a water-repellent pressure sensitive adhesive, and having a tack energy of at least 3.8 N·nm and a tack force of at least 8N, a degree of softness to conform to microreliefs of the skin of the wearer and an elastic modulus at least as low as that of the skin against which the coating is in contact to match the microreliefs and macrodeformations associated with body movement, and a sleeve extending downwardly from a lower edge of the self-adhesive band, the sleeve forming a remaining portion of the compression stocking and being configured to be slipped first on a foot and then on a leg portion of the body member and extend away from the lower edge of the band along an un-banded portion of the leg portion and foot of the body member and to surround the un-banded portion of the leg portion and foot of the body member of the wearer completely, and apply compression to the leg portion.

2. The compression stocking according to claim 1, wherein the textile support structure comprises a lace.

3. The compression stocking according to claim 1, wherein the coating comprises a single-face or double-face, mono- or multi-component coating, with a thickness of about 0.5 mm.

4. The compression stocking according to claim 1, wherein the coating comprises a bi-component coating of two silicone components with a first RTV 833A component, comprising a polydimethylsiloxane with vinyl groups and platinum catalyst, and a second RTV 833B component, with a mixture of polydimethylsiloxanes, sealants and crosslinking agent.

5. The compression stocking according to claim 1, wherein the coating is based on silicone or polyurethane, or styrene-isoprene-styrene or styrene-butadiene-styrene.

6. The compression stocking according to claim 1, wherein moduli G' and G" defined by dynamic mechanical analysis and correlated with tack properties of the coating present a slope of log G'>=0.2 and log G">=0.24.

7. The compression stocking according to claim 1, wherein the self-adhesive band has a thickness of about 1 mm and the coating has a thickness of about 0.5 mm, a grammage of the coating is less than 500 g/m$^2$, and due to porosity of the textile support structure for facilitating curing of the coating, a water vapour transmission rate or permeability is more than 30% higher than that of conventional self-adhesive bands.

8. The compression stocking according to claim 1, wherein the coating is also on an outer surface of the textile support structure.

9. The compression stocking according to claim 1, wherein the self-adhesive band exhibits a compression at 30% elongation of 1.56 hPa/cm.

10. A self-adhesive band of a compression stocking, the compression stocking being configured to be slipped first on a foot and then on a leg portion of a body member to completely surround the leg portion and the foot, consisting of a textile support structure with a tacky coating for securing the band directly to skin of a wearer, the textile support structure comprising an extensible, elastic, aerated, finely knitted or woven textile support structure configured for encircling and providing controlled compression to the body member, and having, at least on an inner surface, said tacky coating configured to be ring shaped when positioned on the body member and consisting of a single, solid, un-interrupted adhesive layer in the form of a film continuously applied and having continuous adhesive properties along a height of the band, the coating comprising a water-repellent pressure sensitive adhesive, and having a tack energy of at least 3.8 N·nm and a tack force of at least 8N, a degree of softness to conform to microreliefs of the skin of the wearer and an elastic modulus at least as low as that of the skin against which the coating is in contact to match the microreliefs and macrodeformations associated with body movement, and the self-adhesive band having a peeling force less than 0.6 N/nm, wherein adhesion of the coating to the skin maintains the compression stocking in place upon the body member without any other attachment means, and the self-adhesive band is removable from the skin without leaving any residue.

11. The self-adhesive band of a compression stocking according to claim 10, exhibiting a compression at 30% elongation of 1.56 hPa/cm.

\* \* \* \* \*